United States Patent [19]
Mackin
[11] Patent Number: 4,784,133
[45] Date of Patent: Nov. 15, 1988

[54] WORKING WELL BALLOON ANGIOSCOPE AND METHOD

[76] Inventor: Robert A. Mackin, 329 W. Granada Ave., Phoenix, Ariz. 85003

[21] Appl. No.: 8,276
[22] Filed: Jan. 28, 1987
[51] Int. Cl.$^4$ .............................................. A61B 17/36
[52] U.S. Cl. ...................................... 128/303.1; 128/6
[58] Field of Search ........................................ 128/4-8, 128/303.1, 395-398; 446/220-222

[56] References Cited

U.S. PATENT DOCUMENTS

| | | | |
|---|---|---|---|
| 4,224,929 | 9/1980 | Furihata | 128/6 |
| 4,418,689 | 12/1983 | Kanazawa | 128/6 |
| 4,445,892 | 5/1984 | Hussein et al. | 128/4 |
| 4,470,407 | 9/1984 | Hussein | 128/6 |

FOREIGN PATENT DOCUMENTS

| | | | |
|---|---|---|---|
| 0178464 | 4/1986 | European Pat. Off. | 128/303.1 |

OTHER PUBLICATIONS

"From Angiography to Angioscopy:Information Discussion", by Cortis et al., "Texas Heart Institute Journal", pp. 281-289, vol. 12, No. 3, Sep. 1986.
"Recanalization of Human Arteries Using Nd-Yag Laser Carried by Optical Fibre" by Geschwind et al., "J. Biomed Eng" 1984, vol. 6, Oct. pp. 281-283.
"Angioscopic Visualization of Pulmonary Emboli", by Moser et al., "Chest", 77:2, Feb. 1980, pp. 198-201.
"Identification of Pulmonary Emboli in the Dog: Comparison of Angioscopy and Perfusion Scanning", by Shure et al., Circulation 64, No. 3, 1981.
"Experimental Intracardiac Visualization", by Gamble et al.
New England Journal of Medicine, vol. 275, No. 25, Jul. 22, 1967, pp. 1397-1403.
Trimedyne's Multi-Lumen Optioscope Brochure.

*Primary Examiner*—Max Hindenburg
*Attorney, Agent, or Firm*—Cahill, Sutton & Thomas

[57] ABSTRACT

A transparent plastic collapsible balloon is attached to the distal end of a flexible bronchoscope or angioscope. The inflatable balloon has a cavity or "working well" at its distal end which communicates by means of a tube with the central channel of the angioscope. Separate channels of the angioscope allow inflation of the balloon after it has been introduced into a vein or artery and visualization of tissue against which the distal end of the balloon is pressed. A laser fiber, forceps, or other instrument can be passed through the central channel of the angioscope, and through an opening in the distal end of the balloon into the working well cavity to allow lasing or other procedures to be performed on tissue abutted by the balloon and isolated by the working well cavity, and to also allow direct visualization of such procedures. Accurate visualization of the operating of lasing, use of the forceps to obtain biopsies or to remove foreign objects, and other intravascular procedures can thereby be achieved.

15 Claims, 2 Drawing Sheets

FIG. 1
(PRIOR ART)
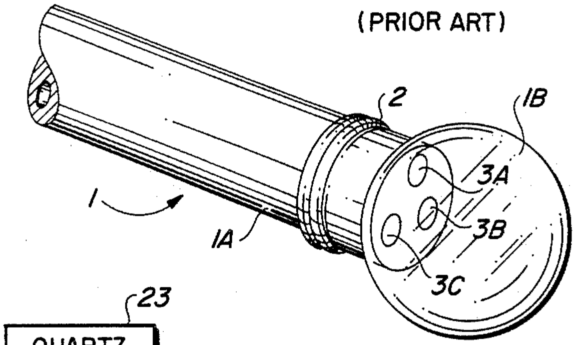
FIG. 3
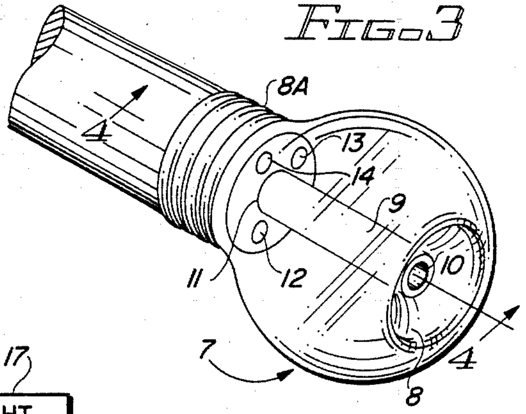
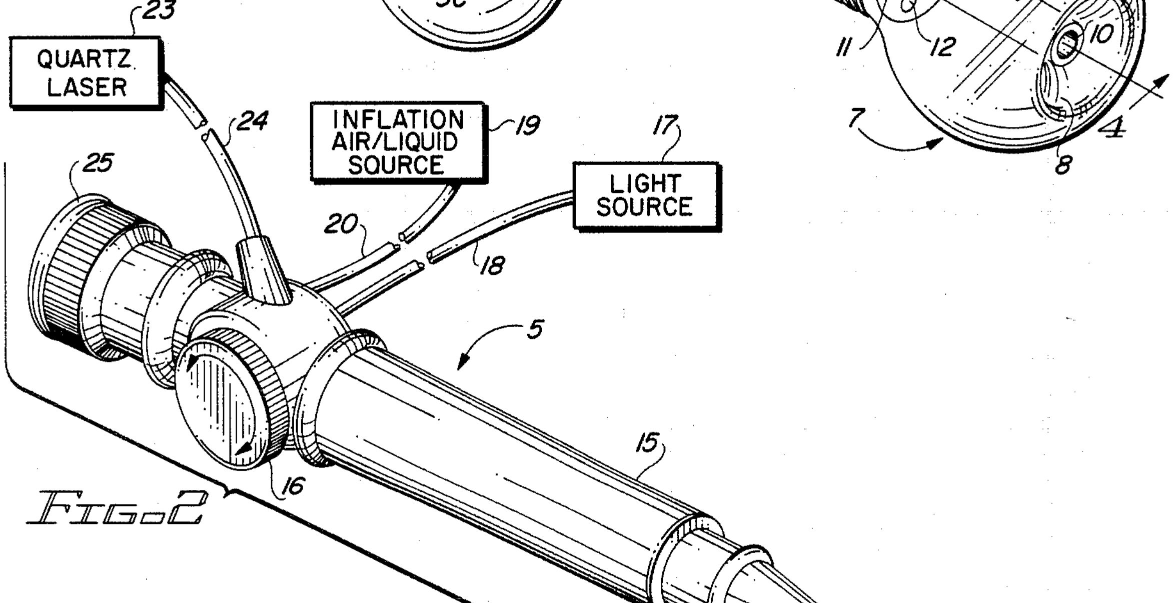
FIG. 2
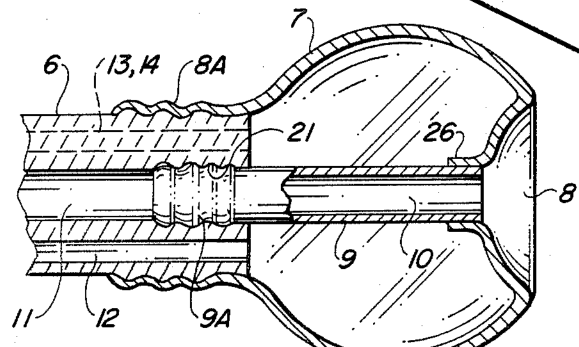
FIG. 4
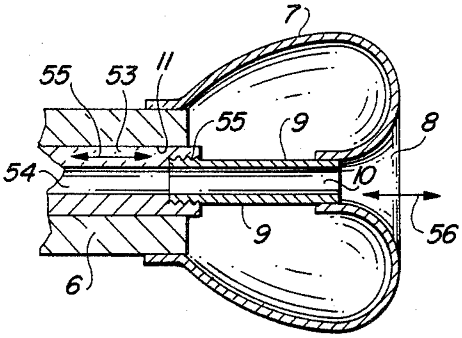
FIG. 12
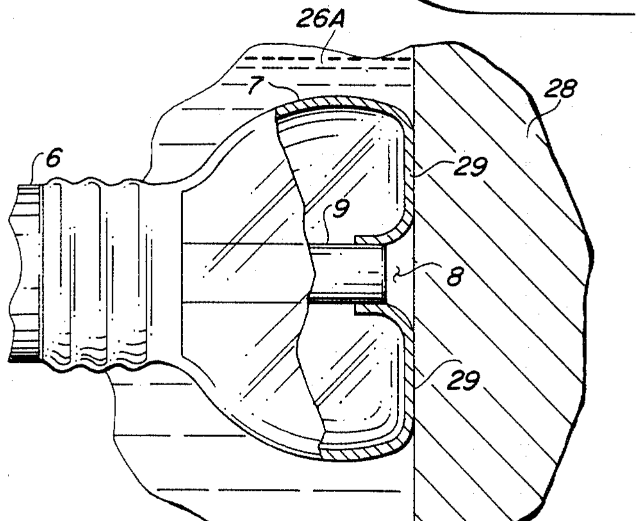
FIG. 5

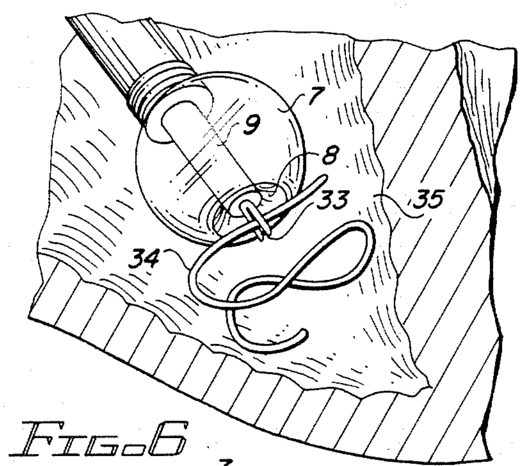
FIG. 6
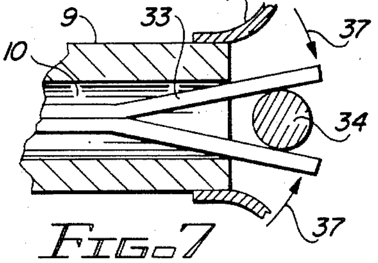
FIG. 7
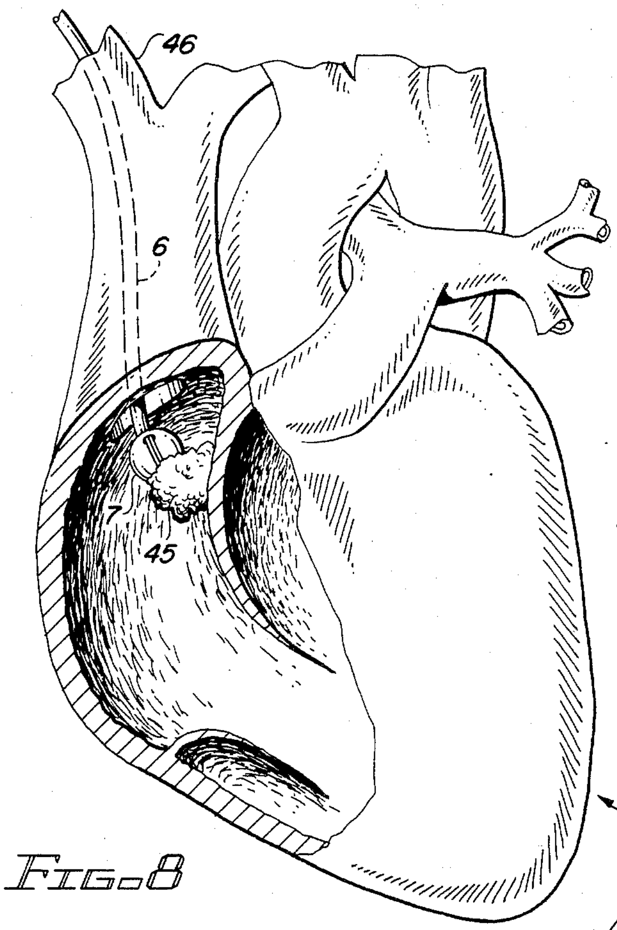
FIG. 8
FIG. 10
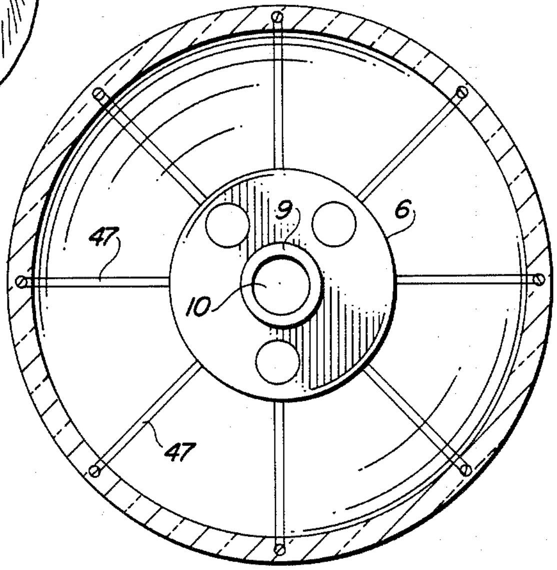
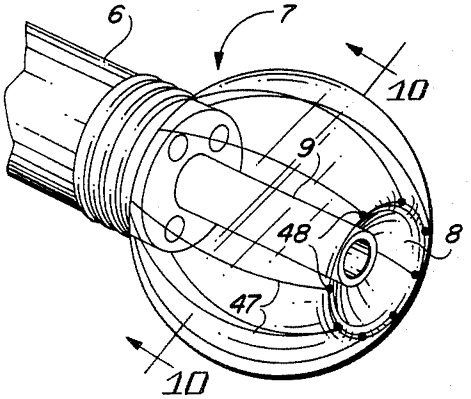
FIG. 9
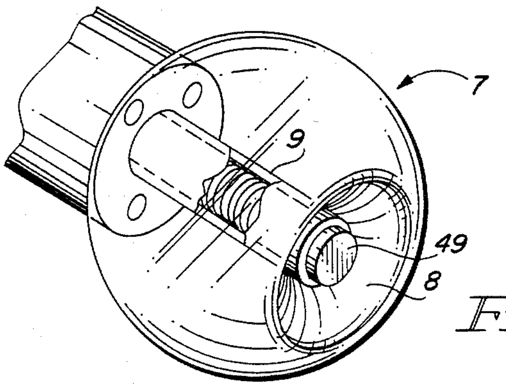
FIG. 11

WORKING WELL BALLOON ANGIOSCOPE AND METHOD

BACKGROUND OF THE INVENTION

The invention relates to angioscopes and procedures using angioscopes, and particularly to an angioscope having on its distal end a transparent balloon having a distal cavity that communicates with a central channel of the angioscope to allow passage of laser fibers, biopsy forceps, or other instrument through the transparent balloon and into the distal cavity.

Fiber optic cardioscopes and angioscopes have been developed to allow visualization of intravascular or intracardiac structures without performing a major surgical procedure such as a thoracotomy to accomplish such visualization. In these devices, an inflatable transparent balloon is attached to the distal end of the cardioscope. After the instrument is inserted into a blood vessel, the balloon is inflated and the instrument is advanced through the vein or artery to the desired location. The inflated balloon serves to displace blood, and when the lumen is occluded or the balloon comes in contact with the endothelium of a vessel or cardiac structure, direct viewing can be accomplished. Originally referred to as cardioscopes, fiber optic cardioscopes have become smaller in diameter and have come to be referred to as angioscopes to reflect their utility in intracardiac and intravascular viewing. More recently, angioscopy has been of use for diagnosis and therapy of systemic, coronary and pulmonary systems. One presently known flexible fiber optic angioscope design, which perhaps is the closest prior art, includes an inflatable end-balloon attached to the distal end of the fiberoptic angioscope. A hollow inflation channel, a light channel, and a viewing channel communicate with the interior of the balloon. Following insertion of the end balloon into a vessel, the balloon is inflated with air or liquid. The balloon serves to occlude a blood vessel or is abutted against an intracardiac structure or the like, and visualization is accomplished. Another design includes an inflatable balloon positioned near but not at the end of the angioscope and is referred to as a near-end-balloon angioscope. After passage of the near-end-balloon angioscope into a vessel, the balloon is inflated, which retards blood flow. A solution such as saline is flushed through a central channel of the catheter to clear blood from the area to be viewed. A third design of prior angioscopes incorporates no balloon in its basic structure. Instead it is passed through a guiding catheter, which itself may or may not have an inflatable balloon, to the area to be viewed. Saline or other solution is flushed to clear the area to be viewed through the guiding catheter or a hollow channel in the angioscope. As a practical matter, the end-balloon angioscope can be used only in diagnosis to allow accurate viewing of intravascular structures, etc., but does not seem adaptable to therapeutic procedures, because biopsy forceps, laser fibers and the like cannot be physically passed through the balloon wall without damaging the balloon. Although laser energy theoretically could be passed through some transparent balloon materials to accomplish certain intravascular procedures, the likelihood of damaging the balloon is high. The near-end-balloon and angioscope without an inflatable balloon both potentially allow for the passage of a laser fiber, biopsy forceps or other instrument to a desired intravascular site. Both these instruments are, however, designed for extracardiac intravascular viewing and have relatively no potential use in intracardiac viewing of lasing, biopsy forcep procedures or the like due to their inability to adequately displace blood from the desired viewing site.

Thus, there remains an unmet need for an improved angioscope structure and method that permit both intracardiac and intravascular visualization, and which also permits accurate lasing, biopsy, or other mechanical procedures to be accomplished on the viewed surface.

SUMMARY OF THE INVENTION

Accordingly, it is an object of the invention to provide a angioscopic structure and technique for accomplishing direct visualization of abutted tissue, and simultaneous performing of laser or other procedures on the visualized area.

It is another object of the invention to provide an angioscopic structure and technique that avoids damage to an inflated end-balloon structure by laser energy or mechanical structure utilized to perform procedures on the visualized area beyond the balloon.

Briefly described, and in accordance with one embodiment thereof, the invention provides an angioscope including a transparent balloon, a flexible catheter having a first channel and second and third channels opening into the interior of the balloon, and a tube extending between the distal end of the first channel, and extending through the transparent balloon, and opening into a region beyond a distal portion of the transparent balloon, an optical fiber passing through the second channel from a light source to produce light that emanates from the distal end of the catheter, an optical fiber and means for effectuating viewing of the region illuminated by the light source, and an apparatus passing through the first channel and the tube to the region beyond the distal portion of the transparent balloon for interacting with tissue or substance illuminated by the light source. In the described embodiment of the invention, a "working well" recess is provide in the distal surface portion of the transparent balloon, the working well recess portion of the balloon including a centered opening into which the tube opens, so that the first channel provides a continuous, open path from a proximal end of the angioscope into the working well recess. After inserting a distal end of the flexible catheter into a vein or artery, the balloon is inflated, either with a gas or a transparent liquid, such as saline solution, and light conducted by the optical fiber through the second channel illuminates the region beyond the distal surface of the transparent balloon. In one described embodiment of the invention, the distal end portion of the inflated balloon is pressed against the wall of an intravascular structure, isolating the working well recess. Saline solution is forced through the first channel and the tube into the working well region to flush out blood therein, allowing clear visualization (through the third channel) of the intravascular wall tissue bounding the working well recess. Various apparatus, such as a laser fiber, biopsy forceps, or tubular means for conducting sufficiently cold liquid to freeze the tissue or other substance adjacent to the working well recess, then may be passed through the first channel and the tube into the working well region. Ablation of the adjacent tissue or substance in the working well recess is thereby accomplished through the first channel and the tube while illumination is accomplished through the second channel and through the wall of the transparent balloon and accurate visualization is accomplished through the third channel and the wall of the transparent balloon. In another embodiment of the invention, accurate visualization of a procedure including retrieving a foreign object by means of a biopsy forceps is achieved.

BRIEF DESCRIPTION OF THE DRAWINGS

FIG. 1 is a partial perspective view of a prior art angioscope.

FIG. 2 is a partial perspective view of a complete angioscope in accordance with the present invention.

FIG. 3 is an enlarged partial perspective view of detail 3 of FIG. 2.

FIG. 4 is a section view along section line 4—4 of FIG. 3.

FIG. 5 is a partial cutaway section view useful in explaining the use of the angioscope of the present invention.

FIG. 6 is a partial perspective cutaway view illustrating utilization of the angioscope of the present invention to retrieve a foreign article.

FIG. 7 is a partial section view useful in explaining the procedure of FIG. 6.

FIG. 8 is a partial perspective cutaway view illustrating utilization of the angioscope of the present invention to perform a biopsy on an intracardiac tumor.

FIG. 9 is a partial perspective view of another embodiment of the angioscope of the present invention.

FIG. 10 is a section view along section line 10—10 of FIG. 9.

FIG. 11 is a partial perspective view of the angioscope in FIG. 3 illustrating introduction of a laser fiber into the working well cavity thereof.

FIG. 12 is a section view of an alternate embodiment of the angioscope of the present invention.

DESCRIPTION OF THE INVENTION

Referring now to FIG. 1, reference numeral 1 designates the end-balloon angioscope previously referred to. The inflatable clear plastic balloon 1B is attached by sutures or other means 2 to a flexible angioscope catheter 1A. Various channels are provided in catheter 1A. For example, an inflation port 3A, a viewing port 3B, and a light channel 3C are provided. This device perhaps represents the closest prior art to the present invention.

In accordance with the present invention, the distal end of a fiber optic angioscope of the present invention is shown in FIGS. 3 and 4. Catheter 6 represents the "flexible fiber optic extension" of the body 15 of angioscope 5. An eye piece 25 enables the physician to view a passage or cavity into which the distal end of angioscope 15 is introduced, and is attached to the proximal end of the body 15 of angioscope 5. An angulation knob 16 controls the axial orientation of the distal tip of catheter 6 relative to body 15 of the angioscope. A laser fiber 24 other instrument can be passed through a biopsy channel 11 of the catheter 6 to allow lasing, biopsy, or other procedure to be performed on tissue or other matter near or at the distal end of catheter 6. Such laser fiber or instrument can be introduced into the channel 11 before or after the catheter 6 is introduced into the vein, artery or other cavity. If this is done, after the catheter is introduced into the body, a clear chamber can be provided at the proximal end of the catheter, into which chamber blood can be drawn through which the instrument can be passed, to ensure that no air bubbles are forced by the instrument through channel 11 into the body.

Reference numeral 19 designates a source of transparent gas or liquid which is forced through tube 20 and channel 13 to inflate balloon 7. Air could be used as a gas, and saline solution could be utilized as a liquid. FIG. 11 shows the end 49 of a laser fiber 24.

In FIG. 2, light source 17 is connected by optical fiber 18 to angioscope 5 and extends through channel 12 of catheter 6 to provide illumination at the distal end of catheter 6. Channel 14 permits viewing of the region beyond the distal end of catheter 6.

In accordance with the present invention, inflatable balloon 7 is attached by sutures 8A the like to the distal end of catheter 6. A recess 8, referred to herein as a "working well", has a central opening therein. The portion of balloon 7 forming that hole is attached by suitable bonding material to a rigid plastic sleeve 9 having passage 10 therethrough that opens into both working well 8 and central passage or "biopsy channel" 11 in catheter 6. The proximal end of tube 9 is threaded into a corresponding threaded area 21 at the distal portion of passage 11 in catheter 6.

In accordance with the present invention, flexible catheter 6 can be introduced in a conventional fashion through a intravascular path, into an intravascular structure or cavity. The balloon is inflated after the distal end of catheter 6 has been introduced into the intravascular structure or cavity. In FIG. 5, reference numeral 26A represents the interior of (for example) a chamber of the heart. Reference numeral 28 designates the endocardium. The distal end of working well balloon 7 is pressed against the surface of endocardium 28, deforming and/or flattening the balloon, as indicated by reference numerals 29. The flattening of the distal end balloon portion surrounding the working well 8 serves to displace blood from the adjacent lining or endocardium of the heart 26A and also serves to isolate the working well area 8 from the surrounding blood pool. Saline or other solution then can be delivered through channel 11 to flush the remaining blood from the working well region 8, making it possible for the physician to easily view the surface of endocardium 28 through catheter 6 and clear plastic balloon 7.

My initial experiments were performed using a working well balloon 7 formed of transparent polyurethane material which was formed by dipping a preshaped glass rod and ball into polyurethane, withdrawing it, and allowing the polyurethane to dry thereon. The glass then was broken free and cleared from the polyurethane. A small opening was made in the recessed working well 8 and a rubber sleeve 9 was secured thereto. The polyurethane balloon was attached to the end of a 4 millimeter Olympus flexible pediatric bronchoscope. A quartz fiber with its sheath was then passed through a one-way valve into and through the biopsy channel 11 of the bronchoscope and through the rubber sleeve 9 into the working well 8.

This device was used in my laser atrial septostomy experiments on two mongrel dogs. An internal jugular vein was used to gain vascular access. An incision large enough to accommodate the working well balloon angioscope catheter 6 was made into the vein wall, and the distal end of the angioscope 5 was inserted. The catheter 6 then was advanced to the superior vena cava and the balloon was inflated to a volume of approximately 2 cubic centimeters. The catheter 6 then was advanced to the interatrial septum, which then was visualized through the viewing port 14 and the distal transparent working well wall of balloon 7.

Nd:YAG laser light at a 40 watt level was delivered over a 2–3 second interval to the atrial septum via the quartz laser fiber. Although difficulties were encountered, including a failure of the material in the working well 8 and collapsing of the balloon 7, which precluded further visualization, laser charring of the visualized tissue was observed during the delivery of laser energy. I expect that if cold saline solution had been used instead of air to cool the quartz fiber during the delivery of the laser energy, the above problem would have been avoided. Saline cooled quartz fiber systems are commercially available, and implementation thereof in the angioscope 5 should present no great difficulty. Another problem observed was that the polyurethane did not collapse satisfactorily because rather sharp edges were created where the polyurethane collapsed on itself. Transparent latex or other material may be more suitable.

Despite the problems encountered in the initial experiments, atrial septoscopy by means of laser energy using an optic angioscope described above appears to be practical and advantageous to existing methods of atrial septostomy.

Other potential applications of the working well balloon angioscope of the present invention include identification of intravascular or intracardiac foreign bodies which require extraction. FIGS. 6 and 7 illustrate this application, wherein a pair of biopsy forceps 33 or the like are introduced beyond the working well 8 of the balloon 7, which allows accurate visualization of the foreign object 34. (Object 34 might be a broken off portion of an endocardial pacemaker lead, catheter, or other object.)

Another potential application of the working well balloon angioscope is the direct visualization of biopsy sites of the myocardium or of a cardiac tumor. FIG. 8 illustrates this application, wherein a cardiac tumor 45 of heart 44 is being visualized via catheter 6 and working well balloon 7. Biopsy forceps such as 33 in FIGS. 6 and could be utilized to remove a bit of tissue from the visualized site.

Another possible application of the working well balloon angioscope is in studies of cardiac arrythmias, wherein a number of thin flexible conductors 47 are embedded in the walls of the balloon 7, as shown in FIG. 9. These conductors 47 pass through a cable in the catheter 6 and terminate upon conductive electrodes 48 located on the outer balloon surface around the perimeter of working well 8, as shown in FIGS. 8 and 10. The electrodes 48 could be utilized to map the endocardium and ascertain the anatomic sites of micro-reentrant and/or ectopic foci. Direct correlation between observed tissue configuration and rhythm disturbance could thereby be achieved. After identification of the the effects arrythmogenic focus, ablation or potential destruction by freezing or heating or by means of electrical, mechanical, chemical or laser energy could be accomplished. As another alternative, some of the electrodes such as 48 in FIG. 9 could be positioned on various other portions of the balloon than on its left or distal end portion. This may be advantageous for recording and mapping of electrical activity within the heart. The electrodes need not actually touch the endocardium, as the electrical signals in the endocardium are transmitted through the blood.

The above-described working well balloon angioscope also may have application in the study of the effects arrythmogenic and antiarrythmogenic substances, which could be instilled or injected through the biopsy channel 11 into the working well region 8 after the distal end of the balloon is abutted against the endocardium, thereby isolating the area which would be contacted by the arrythmogenic or antiarrythmogenic substances. Direct visualization of the site under study can confirm that the working well area has not moved from the intended site being studied.

Other potential applications of the working well balloon angioscope in conjunction with use of laser fibers introduced through the biopsy channel 11 include ablation of accessory (i.e., anomalous) pathways, the atrioventricular node, the His bundle, ectopic foci, hypertrophic (i.e., two thick) myocardium, mural thrombi (i e., intracardiac clots), myxomas (tumors) and treatment of calcified, noncalcified, and congenital valvular stenosis.

An alternate embodiment of the invention is shown in FIG. 12, wherein the threaded left-hand end of the rigid tube 9 is threaded into a threaded hole 55 at the end of a passage 54 through an inner catheter 53 that is slidable within the central channel 11 of outer catheter 6. (The other channels 12, 13, and 14 shown in FIG. 3 also are included in the outer catheter 6 or the inner catheter 53, depending upon the amount of room available and other considerations.) The embodiment of the invention shown in FIG. 12 allows the inner catheter 53 to be moved relative to the outer catheter 6 in the direction of arrows 56. This provides the user with control over the depth of the working well 8, which in some cases might be advantageous.

Thus, an angioscope has been provided with a uniquely designed working well balloon which should have a number of important applications in the study and treatment of cardiovascular diseases While the invention has been described with respect to a number of embodiments, those skilled in the art will be able to make various modifications to the described embodiments without departing from the true spirit and scope of the invention. It is intended that all structures and techniques which are equivalent to those described herein in that they perform substantially the same function in substantially the same way to achieve the same result are to be considered to be within the scope of the invention.

For example, the tube or sleeve 9 can be integral with the balloon, as long as it is sufficiently stiff that the pressure of the inflation gas or liquid does not collapse the channel through the tube or sleeve 9.

I claim:

1. An angioscope comprising in combination:

(a) a flexible catheter having first, second and third channels therein and a proximal end and a distal end;

(b) an inflatable transparent balloon having a first opening and a second opening located opposite to the first opening;

(c) first means for producing a seal between the portion of the transparent balloon around its first opening and the distal end of the catheter;

(d) a tube having a first end connected in communication with a distal end portion of the first channel and having a second end extending through the second opening of the balloon, the second and third channels opening into the interior of the transparent balloon;

(e) a second means for producing a seal between the portion of the transparent balloon around its second opening and the second end of the tube;

(f) third means passing through the second channel for producing light that emanates from the distal end of the catheter;

(g) fourth means passing through the third channel for effectuating viewing of the illuminated region from the proximal end of the catheter; and (h) fifth means passing through the first channel beyond the second end of the tube for interacting with tissue or substance illuminated through the wall of the transparent balloon by the third means and viewed through the fourth means and the wall of the transparent balloon.

2. The angioscope of claim 1 including a working well recess in the surface of a distal portion of the transparent balloon, the second opening being centered in the working well recess.

3. The angioscope of claim 2 including a fourth channel in the catheter opening into the transparent balloon and means for inflating the transparent balloon by passing fluid through the fourth channel.

4. The angioscope of claim 2 wherein the fifth means includes a laser fiber extending through the first channel and extending to the second end of the tube, whereby the visualized tissue or substance can be ablated by a laser beam from the laser fiber.

5. The angioscope of claim 2 wherein the fifth means includes a biopsy forceps instrument with jaws extending beyond the second end of the tube, whereby a sample of the visualized tissue or substance can be removed.

6. The angioscope of claim 4 or 5 including means for forcing clear solution through the first channel into the working well recess in the transparent balloon to flush out blood to allow better visualization of the tissue or substance.

7. The angioscope of claim 2 wherein the first end of the tube is threaded into the distal end portion of the first channel.

8. The angioscope of claim 2 wherein the fifth means includes means for carrying a therapeutic liquid substance to the tissue.

9. The angioscope of claim 8 wherein the therapeutic liquid substance is sufficiently cold to freeze the tissue.

10. The angioscope of claim 2 including a flexible inner catheter slidably disposed in the first channel, the inner catheter having a distal end, a fourth channel extending through the inner catheter, the first end of the tube being connected in communication with the distal end of the fourth channel, wherey the depth of the working well recess of the transparent balloon can be controlled by sliding the inner catheter in the first channel.

11. The angioscope of claim 2 including a plurality of electrodes disposed on the outer surface of the transparent balloon, and a plurality of flexible conductors disposed along the surface of the transparent balloon each flexible conductor extending along the catheter and being connected to a respective electrode, whereby electrical signals can be transmitted to and/or received from tissue or blood contacting the electrodes.

12. An angioscope comprising in combination:

(a) an inflatable transparent balloon;

(b) a flexible catheter having first and second channels therein extending from a proximal end to a distal end thereof, the second channel opening into the interior of the balloon, a proximal portion of the balloon being sealed to a distal end of the flexible catheter;

(c) tubular means for extending from the distal end of the flexible catheter through the balloon to extend the first channel through the balloon so that the extended first channel opens into a region beyond the balloon, a distal portion of the balloon being sealed to a distal end portion of the tubular means;

(d) means passing through the flexible catheter outside of the first channel for producing light that emanates from a distal end of the flexible catheter;

(e) means passing through the catheter outside of the first channel for effecting viewing of the region illuminated by the light producing means; and (f) means passing through the first channel beyond the distal end portion of the tubular means for interacting with tissue or substance beyond the balloon illuminating by the light producing means and viewed through the viewing means.

13. The angioscope of claim 12 including a working well recess in the surface of a distal portion of the transparent balloon.

14. The angioscope of claim 12 including means for inflating the balloon with fluid.

15. The angioscope of claim 12 wherein the tubular means is rigid.

* * * * *